United States Patent
Henderson et al.

(10) Patent No.: US 6,890,960 B1
(45) Date of Patent: May 10, 2005

(54) VETIVER OIL EXTRACTS AS TERMITE REPELLENT AND TOXICANT

(75) Inventors: Gregg Henderson, Saint Gabriel, LA (US); Roger A. Laine, Baton Rouge, LA (US); Donald O. Heumann, Metairie, LA (US); Feng Chen, Baton Rouge, LA (US); Betty C. R. Zhu, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 24 days.

(21) Appl. No.: 09/856,760

(22) PCT Filed: Oct. 18, 2000

(86) PCT No.: PCT/US00/29006

§ 371 (c)(1),
(2), (4) Date: May 23, 2001

(87) PCT Pub. No.: WO01/28343

PCT Pub. Date: Apr. 26, 2001

Related U.S. Application Data

(60) Provisional application No. 60/160,251, filed on Oct. 19, 1999.

(51) Int. Cl.[7] .......................... A01N 35/00; A01N 31/00
(52) U.S. Cl. ....................................... 514/691; 514/729
(58) Field of Search ................................ 514/691, 729, 514/683

(56) References Cited

U.S. PATENT DOCUMENTS

| | | |
|---|---|---|
| 3,835,192 A | 9/1974 | Van Der Linde et al. ............ 260/586 R |
| 4,921,696 A | 5/1990 | Vander Meer et al. ......... 424/84 |
| 4,937,073 A | 6/1990 | Fujikura et al. .......... 424/195.1 |
| 5,303,523 A | 4/1994 | Hand et al. .................... 52/101 |

(Continued)

FOREIGN PATENT DOCUMENTS

| | | | |
|---|---|---|---|
| EP | 1 033 076 A1 | | 5/1999 |
| EP | 1033076 | * | 9/2000 |
| JP | 61033129 | * | 2/1986 |
| JP | 11240802 | | 11/1998 |
| WO | WO 99/25196 | | 5/1999 |
| WO | WO-99/25196 | * | 5/1999 |
| WO | 200027907 | * | 5/2000 |

OTHER PUBLICATIONS

Nishimura et al, Volatile constituents of vetiver oil, 1982, Koryo, vol. 135, pp. 89–95.*
Baxter et al, The hydration of nootkatone in aqueous acids, 1979, Food Chemistry, vol. 4 No. 4, pp. 319–321.*
Adams, R.P., "Cedar Wood Oil—Analyses and Properties," in Modern Methods of Plant Anaysis—Oils and Waxes, H.F. Linskens and J.F. Jackon, eds., Springer Verlag, pp. 159–173 (1991).

(Continued)

*Primary Examiner*—Alton Pryor
(74) *Attorney, Agent, or Firm*—Bonnie J. Davis; John H Runnels

(57) ABSTRACT

Extracts of vetiver oil were found to significantly repel termites. In one extract, nootkatone was isolated and found to be a significant repellent and toxicant of termites. Nootkatone significantly decreased food consumption, decreased tunneling behavior, and increased mortality in termites. Nootkatone is an effective repellent and toxicant of termites either by itself or as an addition to other materials or substrates, including mulches made from vetiver grass roots or other wood products. Nootkatone can also be used to protect construction wood from attack by Formosan subterranean termites. Nootkatone as a repellent is non-toxic to humans and other mammals and is environmentally safe. In addition, α-cedrene was found to be a weak termite repellent; and both zizanol and bicyclovetivenol were found to be repellents and toxicants of termites.

29 Claims, 3 Drawing Sheets

U.S. PATENT DOCUMENTS

| | | | |
|---|---|---|---|
| 5,609,879 A | 3/1997 | Myles | 424/410 |
| 5,802,779 A | 9/1998 | Hulls et al. | 52/101 |
| 5,847,226 A | 12/1998 | Muller et al. | 568/346 |
| 5,874,097 A | 2/1999 | Henderson et al. | 424/405 |
| 2003/0073748 A1 * | 4/2003 | Henderson et al. | 514/691 |

OTHER PUBLICATIONS

Andersen, N.H., "The structures of zizanol and vetiselinenol," Tetrahedron Letters, vol. 21, pp. 1755–1758 (1970).

Andersen, N.H. et al., "Prezizaene and the biogenesis of zizaene," Chemistry and Industry, pp. 62–63 (1971).

Andersen, N., "Biogenetic implications of the antipodal sesquiterpenes of vetiver oil," Phytochemistry, vol. 9, pp. 145–151 (1970).

Cazaussus, A. et al., "GC–MS and GC–MS–MS analysis of a complex essential oil," retrieved from STN–International, accession No. 110:44730 CA XP002159518. Database Chemabs Online: Chemical Abbstracts Service, Columbus, Ohio, US. Abstract & Chromatographia, vol. 25, No. 10, pp. 865–869 (1988). Abstract.

Chen, J. et al., "Determination of feeding preference of Formosan subterranean termite (*Coptotermes formosanus* Shiraki) for some amino acid additives," J. Chem. Ecol., vol. 23, pp. 2359–2369 (1996).

Chen, C. et al., Isolation and identification of 2–phenoxyethanol from a ballpoint pen as a trail–following substance of *Coptotermes formosanus* Shiraki and *Reticulitermes* sp., J. Entomol. Sci., vol. 33, pp. 97–105 (1998).

Chen, J. et al., "Termites fumigate their nests with naphthalene," Nature, vol. 392, pp. 558 (1998).

Coates, R.M. et al., "The crystal structure of khusimol p–bromobenzoate," Chemical Communications, pp. 999–1000 (1969).

Erdtman, H. et al., "The Chemistry of the Natural Order Cupressales XVIII: Nootkatone, a new sesquiterpene type hydrocarbon from the heartwood of *Chamaecyparis nootkatensis* (Lamb.) Spach.," Acta Chem. Scand., vol. 11, pp. 1157–1161 (1957).

Erdtman, H. et al., "The Chemistry of the Natural Order Cupressales 46. The structure of nootkatone", Acta Chem. Scand., vol. 16, pp. 1311–1314 (1962).

Grace, J.K., "Natural resistance of Alaska–cedar, redwood, and teak to Formosan subterranean termites," Forest Products Journal, vol. 44, pp. 41–45 (1994).

Jain et al., "Insect Repellents from Vetiver Oil: I. Zizanol and Epizizanal," Tetrahedron Letters, vol. 23, pp. 4639–4642 (1982).

Kaiser, R. et al., "Biogenetically significant components in vetiver oil," Tetrahedron Letters, vol. 20, pp. 2009–2012 (1972).

Kinyanjui, T. et al., "Potential antitermite compounds from *Juniperus procera* extracts," retrieved from STN–International, accession No. 133:116167 CA XP002159520. See IT: 469–61–4, .alpha.–cedrene & Chemosphere, vol. 41, No. 7, pp. 1071–1074 (2000). Astract.

Lin, Tien–shu et al., "The effects of *Cinnamomum* spp. oils on the control of the termite *Coptotermes formosanus* Shiraki," Taiwan For. Res. Inst. New Series, vol. 10, pp. 459–464 (1995).

Takayasu, "Cockroach Repellent Containing Sesquiterpene," Patent Abstracts of Japan, vol. 1996, No. 07, Jul. 31, 1996 and JP 08 081306 A (Tokiwa), and Database Chemabs Online, retrieved from STN–International, accession No. 125:51527 CA, Chemical Abstracts Service, Columbus, Ohio US. Abstract.

Smadja, J. et al., "Identification of constituents of the essential oil of *Vetiveria zizanioides*," retrieved from STN–International, accession No. 110:218769 CA XP 002159517. Database Chemabs Online: Chemical Abstracts Service, Columbus, Ohio, US. See IT: 5674–50–4–Nootkatone; 28102–79–6, Zizanol & Parfums., Cosmet., Aromes, vol. 84, pp. 61–66 (1988). Abstract.

Vetiver Grass: A Thin Green Line Against Erosion, Board on Science and Technology for International Development, National Research Council, National Academy Press, Washington, D.C. 171 pp. (1993).

Weyerstahl, P. et al., "New sesquiterpene ethers from vetiver oil," Liebigs Ann., pp. 1195–1199 (1996).

Yatagai, M. et al., "Extractives from Yakusugi bogwood and their termiticidal activity ajnd growth regulation effects on plant seeds," reterieved from STN–International, accession No. 115:106318 CA XP002159519. See IT: 469–61–4, .alpha.–cedrene & Mokuzai Gakkaishi, voo. 37, No. 4, pp. 345–351 (1991). Abstract.

XP002159521 Database WPI, Section Ch. Week 199408, Derwent Publications Ltd., London, GB; & JP 06016517 A (Nippon Kayaku KK) Jan. 25, 1994. Abstract.

* cited by examiner

VETIVER OIL EXTRACTS AS TERMITE REPELLENT AND TOXICANT

This is the United States national stage of International Application PCT/US00/29006, filed Oct. 18, 2000; which claims the priority of the filing date of United States provisional patent application Ser. No. 60/160,251, filed Oct. 19, 1999, under 35 U.S.C. 0119(e).

The development of this invention was partially funded by the Government under grant no: USDA/ARS 58-6435-8-084 from the Department of Agriculture. The Government has certain rights in this invention.

TECHNICAL FIELD

This invention pertains to a method to repel subterranean termites using certain extracts of vetiver oil, for example nootkatone, α-cedrene, and a combination of zizanol, and bicyclovetivenol.

BACKGROUND ART

The Formosan subterranean termite, *Coptotermes formosanus* Shiraki, is a major worldwide pest that attacks both living trees and structural wood. Unlike other subterranean termites, the Formosan termite can establish a colony that does not touch the ground.

*Coptotermes formosanus* is native to southeast Asia, but is now also found in Hawaii, along the southeastern Atlantic coast of the United States, and in the Gulf South of the United States. First discovered in the United States by pest control operators in 1965, *C. formosanus* has gradually expanded its geographic domain. The largest single locus of *C. formosanus* in the United States is in south Louisiana, with heavy infestations in Lake Charles and New Orleans. *C. formosanus* may in some case displace native *Reticultermes* spp.

Three principal methods have been used in the past to control *Coptotermes:* (1) chemical and physical barriers to prevent termites from attacking wood, (2) wood preservatives and termiticides used to protect infested or susceptible wood, and (3) destruction of a termite colony by excavation of the nest. See, for example, U.S. Pat. Nos. 4,921,696; 5,303,523; 5,609,879; 5,802,779; and 5,874,097. The extensive use of chemical barriers and termiticides have generated public concern over environmental safety.

The search for a new repellent or termiticide is difficult because studies have shown that termites show unexpected sensitivity to chemicals, sensitivity that differs from that of other insects. For example, phenoxyethanol has been shown to be a trail-following substance; and naphthalene, a toxicant for most insects, was found to be used as fumigant by termites for their nests at concentrations that would kill fire ants. See U.S. Pat. No. 5,874,097; J. Chen et al., "Isolation and identification of 2-phenoxyethanol from a ballpoint pen as a trail-following substance of *Coptotermes formosanus* Shiraki and *Reticulitermes* sp., J. Entomol. Sci., vol. 33, pp. 97–105 (1998); and J. Chen et al., "Termites fumigate their nests with naphthalene," Nature, vol. 392, pp. 558 (1998).

Natural termite repellent chemicals have also been described. The nature leaves of *Cinnamomum osmophloeum* Kaneh, and *C. zeylanicum* B1 have been found to impart termite resistance. The main components of oil extracted from these two species were cinnamic aldehyde and eugenol, respectively, with eugenol exhibiting the greater termite resistance activity. See Tien-shu Lin et al., "The effect of *Cinnamomum* spp. oils on the control of the termite *Coptotermes formosanus* Shiraki," Taiwan For. Res. Inst. New Series, vol. 10, pp. 459–464 (1995). Additionally, the woods of Alaska-cedar, redwood, and teak were found to be resistant to Formosan subterranean termites. Although the termites did feed on the woods, it was only to a very limited extent. See J. K. Grace, "Natural resistance of Alaska-cedar, redwood, and teak to Formosan subterranean termites," Forest Products Journal, vol. 44, pp. 41–45 (1994); and R. P. Adams, "Cedar Wood Oil—Analyses and Properties," in Modern Methods of Plant Analysis—Oils and Waxes, H. F. Linskens and J. F. Jackon, eds., Spring Verlag, pp. 159–173 (1991).

Vetiver grass (*Vetiveria zizanioides*), a fast growing native of India, belongs to the same grass family group that includes maize, sorghum, sugarcane, and lemongrass. Vetiver is used to prevent soil erosion because the roots grow extremely fast. See Vetiver Grass: A Thin Green Line Against Erosion, Board on Science and Technology for International Development, National Research Council, National Academy Press, Washington, D.C. 177pp. (1993). In India, vetiver roots are woven into mats, baskets, fans, sachets, and ornaments. The woven mats are believed to provide protection from insect pests, in addition to their pleasant fragrance. Although the dried roots have been used to repel clothes moths, head lice, and bedbugs, termites are reported to eat vetiver grass. Sugarcane, a member of the same grass family, is even known to be a preferred food of the Formosan subterranean termite. See Vetiver Grass: A Thin Green Line Against Erosion, p. 63 and 81 (1993); and J. Chen et al., "Determination of feeding preference of Formosan subterranean termite (*Coptotermes formosanus* Shiraki) for some amino acid additives," J. Chem. Ecol., vol. 23, pp. 2359–2369 (1996). Despite this knowledge of termite feeding, solid bands of vetiver grass have been speculated to potentially block termites, fire ants, or other insidious underground insects because other insects were known to avoid vetiver oil and vetiver roots. See Vetiver Grass: A Thin Green Line Against Erosion, pp. 24, 28, 80 and 92 (1993).

Vetiver oil extracted from the roots is used in the soap and perfume industry because of its pleasant and persistent fragrance. See U.S. Pat. No. 4,937,073. Vetiver oil is known to be a complex mixture of over 300 compounds, over 150 of which are sesquiterpenoid compounds. See P. Weyerstahl et al., "New sesquiterpene ethers from vetiver oil," Liebigs Ann., pp. 1195–1199 (1996); N. H. Andersen, "The structures of zizanol and vetiselinenol," Tetrahedron Letters, vol. 21, pp. 1755–58 (1970); R. M. Coates et al., "The crystal structure of khusimol p-bromobenzoate," Chemical Communications, pp. 999–1000 (1969). Vetiver oil is known to repel flies and cockroaches. The ingredient in vetiver oil reported to repel insects are the ketones- α-vetivone, β-vetivone, khusimone; and the aldehydes—zizanal, and epizizanal. See Vetiver Grass: A Thin Green Line Against Erosion, p. 80 and 92 (1993); and Jain et al., "Insect Repellents from Vetiver Oil: I. Zizanal and Epizizanal," Tetrahedron Letters, vol. 23, pp. 4639–4642 (1982). Other components of vetiver oil are zizanol (or khusimol), bicyclovetivenol and α-cedrene. See N. Andersen, "Biogenetic implications of the antipodal sesquiterpenes of vetiver oil," Phytochemistry, vol. 9, pp. 145–151 (1970); R. M. Coates et al., "The crystal structure of khusimol p-bromobenzoate," Chemical Communications, Com. 1099, pp. 990–1000 (1969); and R. Kaiser et al., "Biogenetically significant components in vetiver oil," Tetrahedron Letters, vol. 20, pp. 2009–2012 (1972).

Nootkatone, or 4,4a5,6,7,8-hexahydro-6-isopropenyl-4,4a-dimethyl-2(3H)-naphthalenone, is a mildly pungent sesquiterpene ketone found in the oil of Alaska yellow cedar (*Chamaecyparis nootkatensis*) and in a great number of citrus oil, especially oil from grapefruit (*Citrus pavadisi*). Nootkatone is widely used in the perfumery and flavor industries being essentially non-toxic to humans. See U.S. Pat. Nos. 3,835,192 and 5,847,226; H. Erdtman et al., "The Chemistry of the Natural Order Cupressales XVIII: Nootkatone, a new sesquiterpene type hydrocarbon from the heartwood of *Chamaecyparis nootkatensis* (Lamb.) Spach.," Acta Chem. Scand., vol. 11, pp. 1557 (1957); and H. Erdman et al., "The Chemistry of the Natural Order Cupressales 46. The structure of nootkatone," Acta Chem. Scand., vol. 16, pp. 1311 (1962). Nootkatone has also been identified as a minor component of vetiver oil. See U.S. Pat. No. 4,937,073; and N. H. Andersen et al., "Prezizaene and the biogenesis of zizaene," Chemistry and Industry, pp. 62–63 (1971); N. Andersen, "Biogenetic implications of the antipodal sesquiterpenes of vetiver oil," Phytochemistry, vol. 9, pp. 145–151 (1970); and R. Kaiser et al., "Biogenetically significant components in vetiver oil," Tetrahedron Letters, vol. 20, pp. 2009–2012 (1972). The structure of nootkatone is shown below:

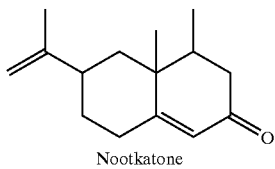

Nootkatone

DISCLOSURE OF INVENTION

We have discovered that certain extracts of vetiver oil are significant repellents and toxicants of termites. We have tested nootkatone, α-cedrene, zizanol and bicyclovetivenol. We have shown that nootkatone significantly decreased food consumption, decreased tunneling behavior, and increased mortality in termites. Nootkatone is an effective repellent and toxicant of termites by itself or as an addition to other substrates, including mulches made from vetiver grass roots or wood products. Nootkatone can also be used to protect construction wood from attack by Formosan subterranean termites. Nootkatone as a repellant is non-toxic to humans and other mammals and is environmentally safe. In addition, α-cedrene was found to be weak termite repellent; and the combination of zizanol and bicyclovetivenol was found to be both a repellant and toxicant of termites.

MODES FOR CARRYING OUT THE INVENTION

Figure 1:
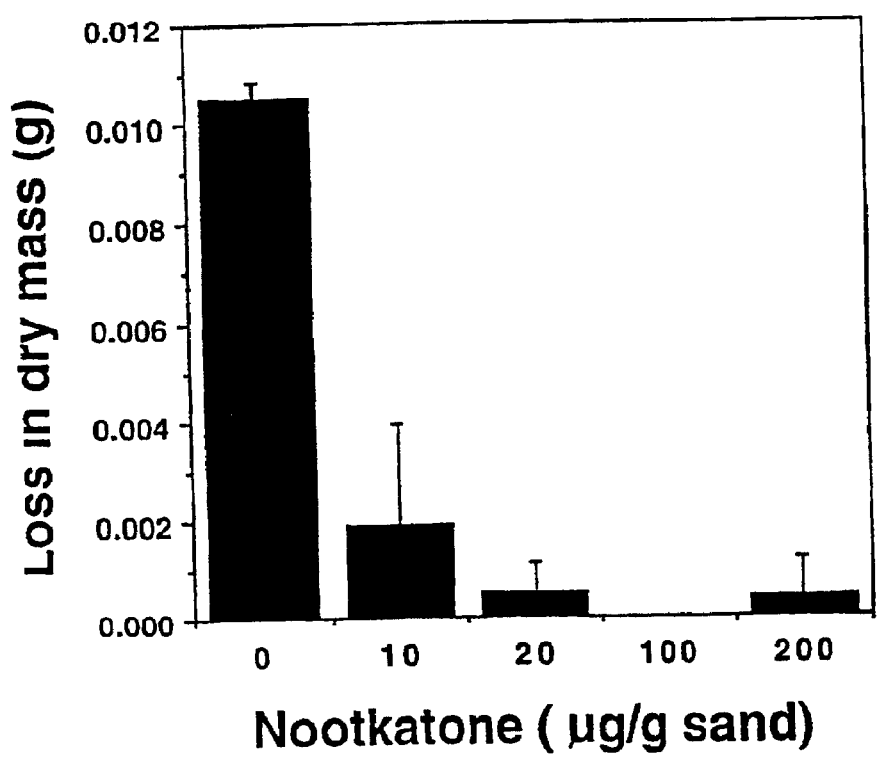
FIG. 1 illustrates the mean consumption of filter paper by termites as the nootkatone concentration in the substrate is increased.

We have discovered that certain extracts of vetiver oil are effective repellents and toxicants of termites. While testing the termite repellence of vetiver grass roots and of vetiver oil isolated from the roots, we developed a bioassay using chambers with treated sand. We tested extracts from vetiver oil that had been separated using a silica gel column eluted with hexane and increasing concentrations of methylene chloride. Four of the five extracts were shown to have termite repellent activity. Upon further analysis of these extracts using gas chromatography/mass spectrometry, nootkatone was found to be a component of one of the termite-repelling extracts from the vetiver oil. Commercially available nootkatone was used to test for repellence against termites. We discovered that nootkatone is an effective repellent and toxicant of termites at concentrations as low as 10 μg/g. Nootkatone reduced feeding and tunneling activity, and caused an increase in mortality in Formosan subterranean termites. Additionally, we found that termites were repelled by commercially-available α-cedrene, a component of vetiver oil. We also isolated and tested for bio-activity extracts from vetiver oil which contained primarily zizanol and bicyclovetivenol; the extracts were shown to be effective repellents and toxicants of termites.

EXAMPLE 1

Extraction of Vetiver Oil from Roots

Vetiver roots from Louisiana grown *Vetiveria zizaniodes* (Donald O. Heumann Greenhouse and Laboratory, Poydras, La.) were cleaned, air-dried, and ground in a blender. The ground roots were stored at −20° C. for 3 to 6 months. After thawing, 5 g of ground vetiver root was added to 300 ml ethyl alcohol, and the mixture stirred for 24 hr at room temperature. About 250 ml alcohol extract was filtered through a 15 cm filter paper and concentrated by a rotor evaporator to approximately 3 ml. The concentrated extract was mixed with 3 g silica gel (60 Angstrom pore) and dried under a hood. A silica column (2×30 cm) was packed with the silica gel containing the vetiver extract packed in the bottom of the column. The compounds of the extract were separated by chloroform running upward overnight in a sealed chamber. The silica gel was then collected one inch at a time for seven fractions total. Each of the seven fractions was extracted with 50 ml ethyl alcohol. Each extract was centrifuged to remove the silica gel, and then concentrated to 3 ml.

Each extract was further separated by thin layer chromatography ("TLC"). Two microliters of each fraction was spotted on the bottom of a silica plate (Silica gel GF, Analtech, Newark, N.J.). Chloroform was used as a solvent for the chromatography. Before the solvent reached the top, the plate was removed and air-dried. The bands on the TLC plate were visualized by charring at 150° C. after spraying with 50% sulfuric acid. At least 1 to 5 bands could be seen in each of the seven fractions. (Data not shown).

EXAMPLE 2

Termite Bioassay of the Extracts From Vetiver Oil

Forty-eight, three-chambered clear plastic containers were used to test the seven extracts from Example 1. Each rectangular chamber (17.5×8×4 cm; Pioneer Packaging Co., North Dixon, Ky.) was divided into three compartments with two inner walls. A small hole (0.5 cm diameter) was melted at the bottom of each of the inner walls to permit termite access to all chambers. The far left chamber was designated the "home compartment" and was filled with 115 g of #4 fine blasting sand (Easy Crete, Inc., Greenwell Springs, La.) to which was added 10 ml distilled deionized water ("ddH$_2$O"). For a food source, a 55 mm #2 Whatman filter paper circle (Whatman International, Maidstone, England)

was weighed and placed in the far right compartment. The center compartment was filled with sand that had been treated with one of the alcohol extracts from Example 1 or with only alcohol (the control). Each of the seven extracts was mixed with ethyl alcohol to a total volume of 25 ml and then added to 115 g #4 blasting sand in a shallow pan. The pan was shaken to evaporate the alcohol prior to adding an additional 575 g sand and mixing. The sand (now 690 g) was left uncovered overnight and re-mixed the following morning. After mixing, 115 g of treated sand and 10 ml ddH$_2$O were placed into the center compartment. Six chambers were prepared using extract from each of the seven fractions for a total of 42 experimental chambers. Six additional chambers for controls received sand treated only with 25 ml ethyl alcohol.

Fifty-five Formosan termites (*Coptotermes formosanus*) (50 workers and 5 soldiers) from a colony collected two months earlier in New Orleans, La., were added to the home compartment of each of the forty-eight containers. The containers were then covered and placed in a dark incubator at 25° C. Containers were examined daily for live termites. Every two to three days, 200 μl ddH$_2$O was added to the filter paper circles. After two weeks, the bottom of each container was scanned and color-printed at actual size using a Hewlett Packard Scan Set 4c and Desk Jet 890C. The filter paper was removal, brushed clean, and air-dried before weighing.

Using the printed images, the total tunnel length in each compartment with sand was measured. One container with extract 7 was excluded from the tunnel length comparisons because the container was inadvertently dropped before scanning the bottom, which broke the termite tunnels.

Between-treatment differences in filter paper weight and tunnel length in home or center compartments were compared by analysis of variance (ANOVA) and Tukey's Studentized Range Test. The results are presented in Tables 1, 2, and 3.

As measured by filter paper consumption, none of the treatments differed significantly from the contact (extract 8). (Table 1) The only significant difference seen among the extracts in filter paper consumption was that treatment with extract 7 showed significantly less filter paper consumption than treatments with extracts 2, 3, or 4.

TABLE 1

Filter Paper Consumption (g)

A. ANOVA results: Dependent Variable = consumption

| Source | DF[a] | Sum of Squares | Mean Squares | F value | Pr > F |
|---|---|---|---|---|---|
| Model | 7 | 0.00071798 | 0.00010257 | 4.19 | 0.0015 |
| Error | 40 | 0.00097939 | 0.00002448 | | |
| Corrected Total | 47 | 0.00169737 | | | |

[a]DF = degrees of freedom

B. Tukey's Studentized Range Test

| Treatment | n | Mean ± S.D. (gm) | Tukey Grouping (α = 0.05) |
|---|---|---|---|
| 2 | 6 | 0.0140 ± 0.0074 | A |
| 4 | 6 | 0.0117 ± 0.0031 | A |
| 3 | 6 | 0.0166 ± 0.0034 | A |
| 5 | 6 | 0.0097 ± 0.0059 | AB |
| 8 (control) | 6 | 0.0093 ± 0.0037 | AB |
| 1 | 6 | 0.0065 ± 0.0048 | AB |

TABLE 1-continued

Filter Paper Consumption (g)

| | | | |
|---|---|---|---|
| 6 | 6 | 0.0053 ± 0.0066 | AB |
| 7 | 6 | 0.0012 ± 0.0020 | B |

As shown in Table 2, there was no significant difference among the treatments in the length of tunnels in the home compartments.

TABLE 2

Tunnel Length in Home Compartment (cm)
ANOVA results: Dependent Variable = Length

| Source | DF[a] | Sum of Squares | Mean Squares | F value | Pr > F |
|---|---|---|---|---|---|
| Model | 7 | 232.242042 | 33.17743465 | 1.73 | 0.1298 |
| Error | 39 | 747.012000 | 19.15415385 | | |
| Corrected Total | 46 | 979.2540425 | | | |

[a]DF = degrees of freedom

As shown in Table 3, there was a strong difference among the treatments in the tunnel length in the center or treated compartment. Tunnel length was significantly less in center compartments treated with either extract 6 or extract 7. These results indicate that the termites were inhibited from tunneling by the compounds found in extracts 6 and 7. Thus vetiver roots contain at least one compound that inhibits tunneling by termites. In the separation techniques described in Experiment 1, the compound(s) separated with the extracts of 6 or 7.

TABLE 3

Tunnel Length in Center Compartment (cm)

A. ANOVA results: Dependent Variable = Length

| Source | DF[a] | Sum of Squares | Mean Squares | F value | Pr > F |
|---|---|---|---|---|---|
| Model | 7 | 4284.6217 | 612.0888 | 39.73 | 0.0001 |
| Error | 39 | 747.012000 | 15.4067 | | |
| Corrected Total | 46 | 4885.4864 | | | |

[a]DF = degrees of freedom

B. Tukey's Studentized Range Test

| Treatment | n | Mean ± S.D. | Tukey Grouping (n = 0.05) |
|---|---|---|---|
| 5 | 6 | 32.6 ± 2.2 | A |
| 3 | 6 | 32.6 ± 3.8 | A |
| 2 | 6 | 32.3 ± 1.9 | A |
| 8 (control) | 6 | 31.2 ± 3.6 | A |
| 4 | 6 | 30.8 ± 1.9 | A |
| 1 | 6 | 28.6 ± 4.4 | A |
| 6 | 6 | 10.6 ± 7.4 | B |
| 7 | 5 | 8.3 ± 2.9 | B |

Thus in the vetiver oil extracts, extract 7 significantly decreased both filter paper consumption and tunneling by termites. Extract 6 significantly decreased the tunneling by termites. Results of all other extracts were not significantly different from the control.

EXAMPLE 3

Isolation of Nootkatone From Louisiana-Grown Vetiver Oil a. Vetiver Oil Extraction Vetiver roots from Louisiana grown *Vetiveria zizanioides* were cleaned, air-dried, ground in a blender and stored at −20° C. One liter of petroleum ether was added to 20 g of dried vetiver roots and stirred for 24 hr at room temperature. The extract was filtered through filter paper and concentrated by rotor evaporator. The oil extract was then redissolved in 5 ml hexane.

b. Isolation of Components of Vetiver Oil

Components of the oil extract were separated using a 2.5×20 cm silica gel column, using a more efficient extraction than in Example 1. Five grams of vetiver oil were dissolved in 50 ml hexane and placed on a silica column that had been washed with 200 ml hexane. The extract was eluted with hexane and an increasing concentration of methylene chloride. Five fractions were isolated: fraction 1 eluted with a ratio of a 20:80 $CH_2Cl_2$: hexane; fraction 2, with a ratio of 30:70; fraction 3, with ratio of 40:60; fraction 4, with a ratio of 60–40; and fraction 5, with a ratio of 80:20. Samples from fractions 1–5 were visualized for their auto-fluorescence under a UV light to indicate the presence of sesquiterpene ketones. The fractions that indicated auto-fluorescence were then further separated by TLC using the method described above in Example 1, along with commercially-available nootkatone.

Using the bioassay as described in Example 2, fractions 1–5 were tested for termite repellent activity. For each fraction, 100 μg/g extract was added to sand and four replicate chambers were established. After a two week incubation, each chamber was analyzed for tunneling activity. Fraction 1 showed no termite bio-activity, while fractions 2–5 showed strong termite repellant activity (low tunneling activity). (data no shown).

The TLC bands 1 and 2 of Fraction 4 were further characterized by Gas chromatography-Mass Spectrometry (GC-MS), using a HP5890 GC/HP 5791 MSD (Hewlett Packard Co., Palo Alto, Calif.). The gas chromatograph separations were performed on a DB-5MS capillary column (30 m×0.25 mm id×0.25 μm, J & W, Folsom, Calif.), using helium (0.8 ml/min) as a carrier gas. The injection port temperature was 250° C. in a spitless mode with 1 μl injection. The initial GC temperature was maintained at 60° C. for 1 min, increased to 150° C. at 2.5° C./min for 15 min and 260° C. at 5° C./min, where it was held for 10 min. The mass spectral detector (MSD) was set on full scan mode (M/Z 41 to 400). Nootkatone was found to be a major constituent of band 2 by comparing the mass spectrum with that of a standard of synthetic nootkatone (crystalline, 97%) purchased from Lancaster Synthesis Inc. (Windham, N.H.) and by comparing the mass spectrum with a known mass spectrum available from a database (Wiley Database, Version 7; Thermoquest-Finnigan, Austin, Tex.).

EXAMPLE 4

Termite Bio-Activity of Nootkatone

The amount of nootkatone isolated from the vetiver oil was insufficient to test for termite repellant activity. Nootkatone was therefore purchased from a commercial source (Lancaster Synthesis Inc., Windham, N.H.). A three-chambered plastic container was used as described above in Example 2. A small hole was melted at the bottom of each of the two inner walls to connect the chambers. Four replicate chambers were used for each concentration of nootkatone (μg/g of sand) tested: 0, 10 μg/g, 20 μg/g, 100 μg/g, and 200 μg/g. For each concentration, the nootkatone in 25 ml ethyl alcohol was mixed with 500 g #4 blasting sand as described in Example 2. The sand was dried overnight. The next day, 115 g of treated sand was added to the middle chamber; 115 g untreated sand was added to one end chamber, and a weighted filter paper (Whatman #1, 55 mm) was placed in the opposite end chamber. The filter paper had been dried at 70° C. for 3 hr and cooled to room temperature before weighing. Then 10 ml $ddH_2O$ was added to each chamber with sand and 200 μl $ddH_2O$ was added to the filter paper. Four containers with no nootkatone served as negative controls. Fifty worker and 5 soldier termites from a single colony collected in Algiers, La., were placed in each untreated sand chamber. The chambers were covered and kept in a dark incubator at 29° C.

On the $16^{th}$ day, the number of live termites was counted, and the bottom of each container was scanned to determine tunneling length as described in Example 2. The filter paper from each container was removed, cleaned, dried at 70° C. for 3 hr, cooled, and finally weighed.

Between-treatment differences in filter paper weight, mortality, and tunnel length in the treated compartments were compared by analysis of variance (ANOVA) and Tukey's Studentized Range Test. The results are presented in Tables 4, 5, and 6 and in FIGS. 1–3.

Consumption was calculated as the difference between the weight of filter paper before and after the incubation. FIG. 1 and Table 4 show that the mean consumption of filter paper decreased significantly with nootkatone concentration. In control experiments, termites tunneled through the middle compartment to the filter paper in the end compartment. Even at the lowest concentration, nootkatone significantly decreased feeding as measured by loss of filter paper weight from the control. Almost no consumption of filter paper was seen at concentrations higher than 20 μg/g. As shown below, this decrease in feeding was due both to a decrease in tunneling through the middle chamber and to an increase in mortality of the termites.

TABLE 4

Filter Paper Consumption (g)

A. ANOVA results: Dependent Variable = consumption

| Source | $DF^a$ | Sum of Squares | Mean Squares | F value | Pr > F |
|---|---|---|---|---|---|
| Model | 4 | 0.00031693 | 0.00007923 | 9.39 | 0.0005 |
| Error | 15 | 0.00012662 | 0.00000844 | | |
| Corrected Total | 19 | 0.00044355 | | | |

$^a$DF = degrees of freedom

B. Tukey's Studentized Range Test

| Treatment | n | Mean ± S.D. (gm) | Tukey Grouping (α = 0.05) |
|---|---|---|---|
| 1 (control) | 4 | 0.010500 ± 0.005867 | A |
| 2 (10 μg/gm) | 4 | 0.001900 ± 0.002641 | B |
| 3 (20 μg/gm) | 4 | 0.000525 ± 0.000709 | B |
| 4 (100 μg/gm) | 4 | 0.000025 ± 0.000050 | B |
| 5 (200 μg/gm) | 4 | 0.000275 ± 0.000550 | B |

Figure 2:
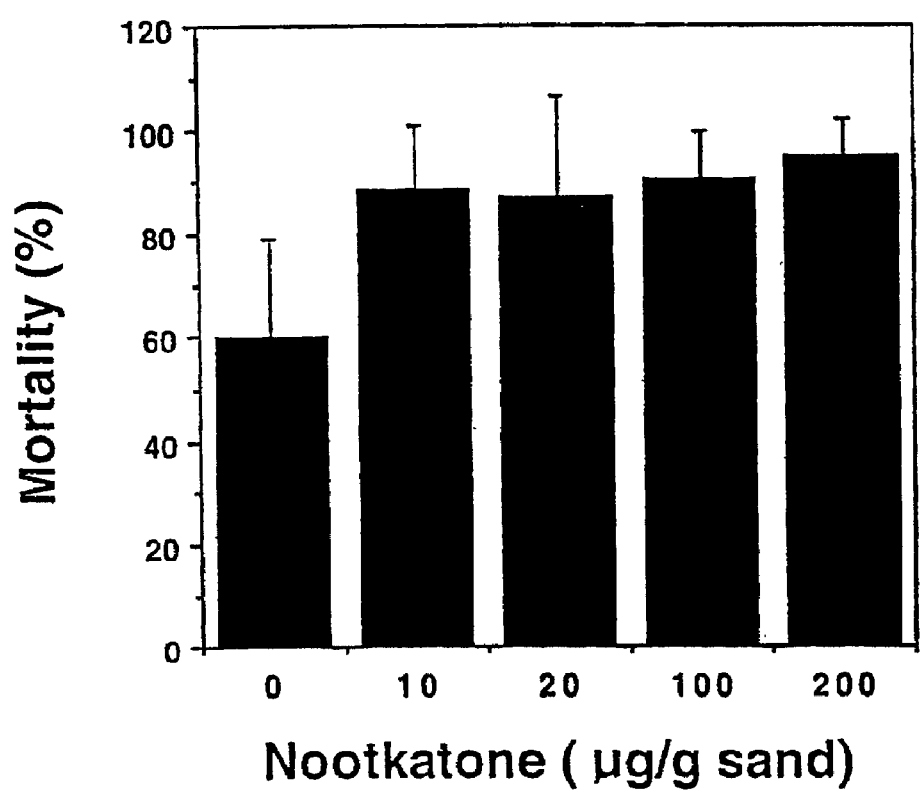
FIG. 2 illustrates the next mortality of termite workers and soldiers as the nootkatone concentration in the substrate is increased.

FIG. 2 and Table 5 show mortality of only workers. Because of the low number of soldiers added to the containers, the soldier data was excluded. Mortality between the treatments and control was significantly different. Ninety percent mortality or greater was seen in all chambers where the nootkatone concentration was ≦100 μg/g sand.

TABLE 5

Worker Mortality

A. ANOVA results: Dependent Variable = Length

| Source | DF[a] | Sum of Squares | Mean Squares | F value | Pr > F |
|---|---|---|---|---|---|
| Model | 4 | 3370.8000 | 842.7000 | 4.22 | 0.0174 |
| Error | 15 | 2993.0000 | 199.5333 | | |
| Corrected Total | 19 | 6363.8000 | | | |

[a]DF = degrees of freedom

B. Tukey's Studentized Range Test

| Treatment | n | Mean ± S.D. | Tukey Grouping ($\alpha$ = 0.05) |
|---|---|---|---|
| 1 (control) | 4 | 58.50 ± 18.72 | B |
| 2 (10 μg/gm) | 4 | 88.50 ± 10.12 | A |
| 3 (20 μg/gm) | 4 | 87.00 ± 18.22 | A |
| 4 (100 μg/gm) | 4 | 90.50 ± 11.70 | A |
| 5 (200 μg/gm) | 4 | 95.00 ± 8.718 | A |

Figure 3:
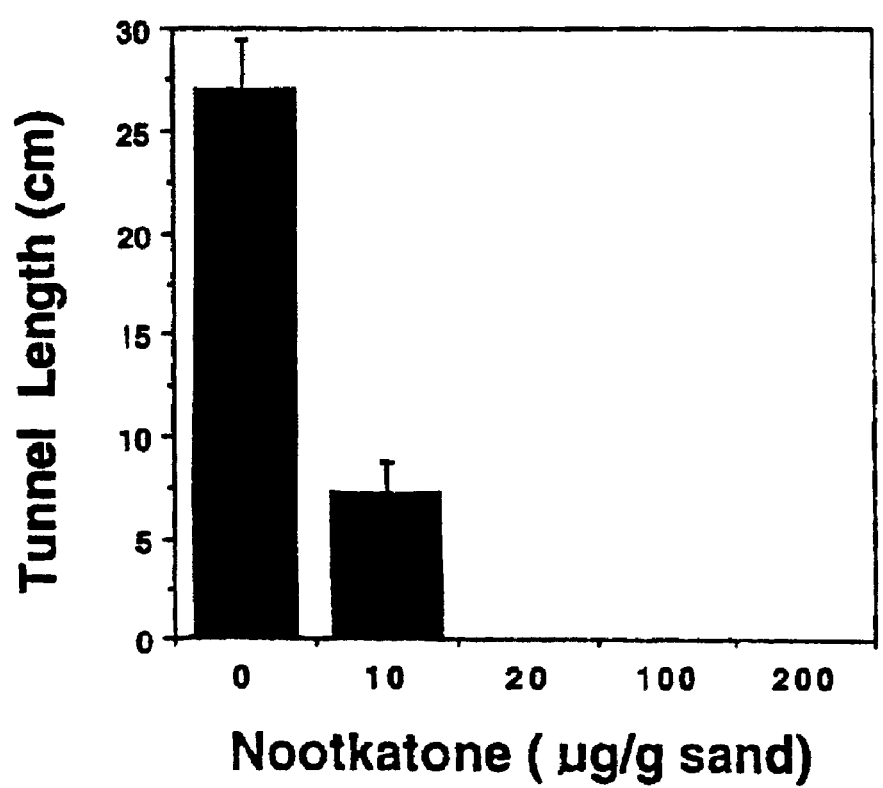
FIG. 3 illustrates the mean tunnel length dug by termites as the nootkatone concentration in the substrate is increased.

FIG. 3 and Table 6 show the length of all tunnels seen in the middle or treated chamber at the end of the 16$^{th}$ day. The presence of nootkatone substantially decreased the tunneling activity at the lowest concentration of 10 μg/g. At higher concentrations of nootkatone, no tunneling was visible in the middle chamber.

TABLE 6

Tunnel Length in Treated Compartment (cm)

A. ANOVA results: Dependent Variable = Length

| Source | DF[a] | Sum of Squares | Mean Squares | F value | Pr > F |
|---|---|---|---|---|---|
| Model | 4 | 2187.722 | 546.9305 | 43.1 | 0.0001 |
| Error | 15 | 190.3475 | 12.6898 | | |
| Corrected Total | 19 | 2378.0695 | | | |

[a]DF = degrees of freedom

B. Tukey's Studentized Range Test

| Treatment | n | Mean ± S.D. | Tukey Grouping ($\alpha$ =0.05) |
|---|---|---|---|
| 1 (control) | 4 | 27.000 ± 6.072 | B |
| 2 (10 μg/gm) | 4 | 7.225 ± 5.155 | A |
| 3 (20 μg/gm) | 4 | 0.000 ± 0.000 | A |
| 4 (100 μg/gm) | 4 | 0.000 ± 0.000 | A |
| 5 (200 μg/gm) | 4 | 0.000 ± 0.000 | A |

These results show that nootkatone at concentrations as low as 10 μg/g decreased tunneling and feeding of termites, and increased mortality. Thus nootkatone was shown to be a potent termite repellent and toxicant. It is believed that concentrations between 10 μg/g and 1000 μg/g, more preferably between 10 μg/g and 200 μg/g, will be useful in repelling and killing termites.

EXAMPLE 5

Termite Bio-Activity of α-Cedrene

The termite bio-activity of α-cedrene, a component of vetiver oil, was tested using a commercially available product (Fluka, a division of Sigma-Aldrich, Inc., St. Louis, Mo.). A new method for screening compounds for termite bio-activity was developed that was faster than the bioassay described in Example 2. Five cm diameter petri dishes with lids were used. Two ml of hot agar solution (1.5 g/100 ml ddH$_2$O) was spread evenly in the bottom of each dish and allowed to cool. The agar solution provided moisture for the termites and held the sand in place. The sand was autoclaved for 30 min, the alcohol with sample added, and dried in an oven. For three dishes, one half of the bottom of each dish was covered with 1.5 g treated sand mixed with a total of 100 μg α-cedrene per dish, dissolved in 250 μl ethanol, and the other half with 1.5 g untreated sand (only ethanol). The sand completely covered the agar, but was not thick enough to conceal tunneling termites. Three dishes were prepared as a control with only untreated sand in each side. Finally, ten termites were added to each dish, and the dishes were covered to eliminate light.

The termite distribution in each dish, measured by counting the number of termites on the untreated half of the dish, was examined each hour for up to 8 hr. A Chi-Square test indicated that when 23 or more of the 30 termites (mean value of all replicates) or at least 76.7% were observed on the untreated sand, there was a significant difference of termite distribution between the treated group and the control group ($X^2$=4.59, df=1; p=0.032; SAS Institute, 1998). Therefore the extract was considered a repellent. The extract was considered toxic if some or all termites behaved sluggishly, were moribund or dead.

The results for α-cedrene are shown below in Table 7. α-Cedrene was a weak repellent for termites at a concentration of 100 μg/dish, at least in the 2–3 h time frame. None of the termites died in any of the dishes.

TABLE 7

Activity of α-Cedrene (100 μg/dish):
Percent of termites on the untreated side (sum of the three replicates)

| | 1 hr | 2 hr | 3 hr | 4 hr | 24 hr |
|---|---|---|---|---|---|
| Control | 60 | 20 | 53.3 | 53.3 | 56.7 |
| α-Cedrene | 50 | 93.3 | 86.7 | 63.3 | 63.3 |

EXAMPLE 6

Termite Bio-Activity of Vetiver Oil Extracts Comprising Zizanol and Bicyclovetivenol Extracts of Louisiana grown vetiver oil were prepared as described in Example 3, using a silica gel column and TLC. Fractions with high bio-activity were analyzed with GC-MS. Fractions with high bio-activity were analyzed with GC-MS and found to have high concentrations of zizanol and bicyclovetivenol as described in Example 3. The fractions having high concentrations of zizanol and bicyclovetivenol were identified by comparing the mass spectrum with a known graph available from a database. From this information, extracts with higher concentrations of zizanol and bicyclovetivenol were prepared and analyzed for termite bio-activity using the quick petri dish method as described in Example 5.

In one experiment, two different extractions were compared to a control using four replicates of each experimental condition. In Extract A, the bicyclovetivenol peak was found by GC-MS to be twice the height of the zizanol peak. In Extract B, the reverse was true. Each extract was tested at two concentrations, 100 μg/dish and 500 μg/dish. At these two concentrations, both extracts showed termite activity as repellants and mild toxicants as shown in Table 8. There was no difference between the efficacy of the two extracts noted in this experiment, even though the relative amounts of zizanol and bicyclovetivenol were reversed between the two extracts. This is some evidence that zizanol and bicyclovetivenol individually have termite bio-activity.

TABLE 8

Bio-Activity of Vetiver Oil Extracts Comprising Primarily Zizanol and Bicyclovetivenol; (An Average Percentage of Termites on the Untreated Side for Four Replicates)

| Sample | 1 hr | 2 hr | 3 hr | 4 hr | 5 hr | 24 hr | 48 hr |
|---|---|---|---|---|---|---|---|
| Control | 50 | 50 | 52.5 | 47.5 | 55 | 57.5 | 40 |
| Extract A | | | | | | | |
| 100 µg/dish | 50 | 52.5 | 75 | 75 | 87.5 | 95 | 95 |
| 500 µg/dish | 77.5 | 77.5 | 92.5 | 95 | 85 | 92.5** | 95** |
| Extract B | | | | | | | |
| 100 µg/dish | 45 | 47.5 | 75 | 72.5 | 70 | 75 | 62.5 |
| 500 µg/dish | 52.5 | 67.5 | 75 | 85 | 80 | 97.5** | 100** |

**Termites were aggregated and moribund.

Another experiment was conducted to test a higher concentration. Extract C was similar to Extract B, with the zizanol peak about twice the size of the bicyclovetivenol peak on the GS. Six replicates were run for both the controls and the treated samples (0.86 mg extract/dish). The results are shown in Table 9. Termites were moribund by 24 hr, and began dying at 48 hr. By 7 days, 80% of the termites in the treated dishes had died, while only two control termites had died.

TABLE 9

Bio-Activity of Vetiver Oil Extracts Comprising Primarily Zizanol and Bicyclovetivenol; An Average Percentage of Termites on the Untreated Side for Six Replicates or [Percent Mortality]

| | 1 hr | 3 hr | 5 hr | 24 hr | 48 hr | 3 d | 4 d | 7 d |
|---|---|---|---|---|---|---|---|---|
| Control* | 50 | 55.9 | 45 | 47.2 | 54.4 | 55.6 | 48.5 | 43.5 |
| 0.86 mg/dish | 63.3 | 73.3 | 51.7 | 75 | [15] | [36.7] | [46.7] | [80] |

*Two termites died in the 6 control dishes.

This experiment indicated that at a higher concentration, the extracts of vetiver oil comprising primarily zizanol and bicyclovetivenol were both termite repellants and toxicants.

EXAMPLE 7

Toxicity of Nootkatone

To further determine the level of toxicity of nootkatone on Formosan subterranean termites, a toxicity experiment will be conducted. Termites will be placed in sealed containers that contain a sand substrate. In three sets of containers the sand will be treated with nootkatone at levels of 10 µg/g, 100 µg/g, and 200 µg/g of sand, respectively. The fourth container will be a control with no nootkatone. Daily counts of dead termites over a one-week period will be made to determine mortality for each treatment. Termites generally live seven days without food. It is expected that mortality will increase as the concentration of nootkatone increases.

EXAMPLE 8

Repellence and Toxicity of Wood Treated with Nootkatone

To demonstrate the effectiveness of nootkatone in repelling Formosan subterranean termites from construction wood, a termite feeding and tunneling experiment was conducted to compare wood treated with nootkatone, vetiver oil, and disodium octaborate tetrahydrate (TIM-BOR®, U.S. Borax, Inc., Valencia, Calif.). Balsa wood (5 cm×5 cm×0.5 mm) was soaked for 1 hr in a 1% ethanol solution of either vetiver oil, nootkatone, TIM-BOR®, or an ethanol control. The treated wood was then dried and allowed to air until used in the experiments. The experiments were run at one, three, and six months after the wood was treated. The feeding and tunneling experimental procedure was as described in Example 2, except that in place of the filter paper as food for the termites, treated balsa wood was placed in each end compartment; and untreated sand was placed in all three chambers. Into the center chamber was added 225 workers and 25 soldiers collected from two large Formosan termite colonies in New Orleans, La. Three replicate containers for each of the two colonies and for each treatment of balsa wood were monitored for 8 days. Tunneling activity was periodically checked on days 3, 5, and 7 by scanning the bottoms of the containers. On day 8, the balsa wood was removed and weighed to determine wood consumption. At all three time periods, termites in the three experimental groups consumed less wood than the control group, with nootkatone having the greatest effect on decreasing wood consumption at the 1 and 3 month interval. Even at six months, nootkatone and vetiver oil were as effective as the borate solution in reducing wood consumption. (Data not shown). Tunneling activity of the termites was substantially reduced with vetiver oil and especially with nootkatone, even after three months. TIM-BOR® did not show an effect on tunneling behavior. (Data not shown) Both nootkatone and vetiver oil retained their effectiveness as a termite repellent six months after the initial treatment of the wood sample. (Data not shown).

These compounds, i.e., nootkatone, α-cedrene, zizanol and bicyclovetivenol, which are effective as termite repellents or toxicants could be added to any substrate or material to protect the material from termite infestation or damage, including, but not limited to, any cellulose-containing materials, soil, diatomaceous earth, and even incorporated into plastics.

In the specification and the claims, an "effective amount" of a compound, e.g., nootkatone, α-cedrene, zizanol and bicyclovetivenol, is an amount that, when applied to a substrate or other material, causes significant repellence or toxicity, or that decreases the activity or viability of termites as compared to an otherwise identical environment without the added extract.

The complete disclosures of all references cited in this specification are hereby incorporated by reference. Also incorporated by reference is the complete disclosure of the following unpublished manuscript: B. Zhu et al., "Nootkatone is a repellent for Formosan subterranean termites (*Coptotermes formosanus*;" accepted and re-submitted to Journal of Chemical Ecology in October 2000; L. Maistrello et al., "Effects of nootkatone and a borate compound on Formosan subterranean termite and its symbiont protozoa," submitted to Journal of Entomological Science in May 2000; and B. Zhu et al., "Evaluation of vetiver oil and seven insect-active essential oils against Formosan Subterranean Termites," submitted to the Journal of Chemical Ecology in September 2000; L. Maistrello et al., "Effects of vetiver oil and its consitutents on *Coptotermes formosanus* and its symbiotic fauna," poster presentation at XXI International Congress of Entomology, Iguassu Falls, Brazil, Aug. 20–26, 2000; and the complete text of U.S. provisional application Ser. No. 60/160,251, filed Oct. 19, 1999. In the event of an otherwise irreconcilable conflict, however, the present specification shall control.

What is claimed:

1. A method for protecting a material from termite infestation, comprising treating the material with a composition comprising an effective amount of a compound selected from the group consisting of nootkatone, zizanol, and bicyclovetivenol, wherein said composition is free of vetiver oil, wherein said material without said treatment is susceptible to termite infestation, and wherein the treated material repels or kills termites substantially more than does an otherwise identical material that has not been treated with the compound.

2. A method as in claim 1, wherein the treated material repels termites.

3. A method as in claim 1, wherein the treated material kills termites.

4. A method as in claim 1, wherein the material to be treated is selected from a list consisting of soil, substrate, plastics, diatomaceous earth, and a cellulose-containing materials.

5. A method as in claim 1, wherein the compound is nootkatone.

6. A method as in claim 1, wherein the compound is zizanol.

7. A method as in claim 1, wherein the compound is bicyclovetivenol.

8. A method as in claim 1, additionally comprising treating the material with a one or more different compounds selected from the group consisting of nootkatone, α-cedrene, zizanol and bicyclovetivenol.

9. A composition for a protective barrier against termite infestation, said barrier composition comprising an effective amount of a compound selected from the group consisting of nootkatone, zizanol and bicyclovetivenol, and a substrate material selected from the group consisting of mulch, soil, and diatomaceous earth, wherein said composition is free of vetiver oil and wherein such treated barrier repels or kills termites substantially more than does an otherwise identical barrier that has not been treated with the compound.

10. A composition as in claim 9, wherein the substrate material is a mulch.

11. A composition as in claim 10, wherein the mulch is dried vetiver grass.

12. A composition as in claim 10, wherein the mulch is a cellulose-containing material.

13. A composition as in claim 9, wherein the substrate material is soil.

14. A composition as in claim 9, wherein the substrate material is diatomaceous earth.

15. A composition as in claim 9, wherein the compound is nootkatone.

16. A composition as in claim 15, wherein the concentration of nootkatone in said barrier is between about 10 µg/g and about 1000 µg/g.

17. A composition as in claim 15, wherein the concentration of nootkatone in said barrier is between about 10 µg/g and about 200 µg/g.

18. A composition as in claim 9, wherein the compound is zizanol.

19. A composition as in claim 9, wherein the compound is bicyclovetivenol.

20. A composition as in claim 9, additionally comprising one or more different compounds selected from the group comprising nootkatone, α-cedrene, zizanol and bicyclovetivenol.

21. A composition for a protective barrier against termite infestation, said barrier composition comprising an effective amount of a compound selected from the group consisting of nootkatone, zizanol, and bicyclovetivenol, and a construction wood, wherein said construction wood without said compound is susceptible to termite infestation, wherein said composition is free of vetiver oil and wherein the treated construction wood repels or kills termites substantially more than does an otherwise identical construction wood that has not been treated with the compound.

22. A composition as in claim 21, wherein the compound is nootkatone.

23. A composition as in claim 22, wherein the concentration of nootkatone in said barrier is between about 10 µg/g and about 1000 µg/g.

24. A composition as in claim 22, wherein the concentration of nootkatone in said barrier is between about 10 µg/g and about 200 µg/g.

25. A composition as in claim 21, wherein the compound is zizanol.

26. A composition as in claim 21, wherein the compound is bicyclovetivenol.

27. A composition as in claim 21, additionally comprising one or more different compounds selected from the group consisting of nootkatone, α-cedrene, zizanol and bicyclovetivenol.

28. A composition for a protective barrier against termite infestation, said barrier composition comprising an effective amount of a compound selected from the group consisting of zizanol and bicyclovetivenol, and a substrate material, wherein said substrate material without said compound is susceptible to termite infestation, wherein said composition is free of vetiver oil, and wherein such treated barrier repels or kills termites substantially more than does an otherwise identical barrier that has not been treated with the compound.

29. A composition as in claim 28, additionally comprising one or more different compounds selected from the group consisting of nootkatone, α-cedrene, zizanol and bicyclovetivenol.

* * * * *